United States Patent [19]

Schleifstein

[11] Patent Number: 4,959,500
[45] Date of Patent: Sep. 25, 1990

[54] POLYBROMINATED BIS SULFONAMIDES

[75] Inventor: Robert A. Schleifstein, Baton Rouge, La.

[73] Assignee: Ethyl Corporation, Richmond, Va.

[21] Appl. No.: 355,558

[22] Filed: May 23, 1989

[51] Int. Cl.$^5$ ............................................. C07C 143/78
[52] U.S. Cl. ....................................... 564/82; 524/169
[58] Field of Search ..................................... 564/82, 90

[56] References Cited

U.S. PATENT DOCUMENTS

| 2,809,210 | 10/1957 | Short et al. | 564/82 |
| 4,123,411 | 10/1978 | Coran | 524/169 |
| 4,218,357 | 8/1980 | Mark et al. | 524/169 |
| 4,254,015 | 3/1981 | Thomas et al. | 524/169 |
| 4,399,246 | 8/1983 | Hyde | 524/169 |
| 4,486,560 | 12/1984 | Dromas | 524/169 |
| 4,745,143 | 5/1988 | Mason et al. | 524/169 |

FOREIGN PATENT DOCUMENTS 51-46089 12/1976 Japan .

OTHER PUBLICATIONS

CAS Registration 2654-77-5 and 2654-68-4.
Chemical Abstract 101(25):230066j.
Chemical Abstract 94(9):65359j.
Chemical Abstract 85(23):17002h.
Chemical Abstract 82(23):155946e.
Chemical Abstract 66(9):37571a.
Chemical Abstract 66(3):10128Z.
Chemical Abstract 64:8383f.
Chemical Abstract 58:5671e.
Chemical Abstract 58:3341c.

Primary Examiner—Veronica P. Hoke
Attorney, Agent, or Firm—John F. Sieberth; David E. LaRose

[57] ABSTRACT

Described are polybromoaromatic bis-sulfonamides containing at least two bromoaromatic groups, from 18 to 30 carbon atoms (preferably 18 to 24), and from 6 to 14 bromine atoms substituted on the aromatic rings. Such polybromoaromatic bis-sulfonamides may be represented by the general formula

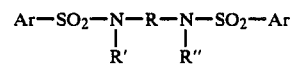

where Ar are the same or different polybromoaromatic groups, R is a divalent aromatic or bromoaromatic group, and R' and R" are independently hydrogen atoms, hydrocarbon groups or halohydrocarbon groups in which the halogen atoms are chlorine or bromine, the total number of bromine atoms substituted on the aromatic rings of the groups designated as Ar and R falling in the range of 6 to 14. These sulfonamides are useful as flame retardants and plasticizers for thermoplastic polymers and have the advantage of relatively low volatilities at polymer processing temperatures.

8 Claims, No Drawings

POLYBROMINATED BIS SULFONAMIDES

This invention provides certain novel polybrominated aromatic sulfonamides useful as flame retardants and plasticizers for thermoplastic polymers and the like. This invention also provides novel flame retarded thermoplastic compositions having improved melt flow characteristics by virtue of the incorporation therein of these sulfonamide additives. The sulfonamides of this invention have relatively low volatilities at polymer processing temperatures and thus minimize the extent to which the additive is vaporized during polymer processing. This in turn reduces the extent to which ambient air quality is impaired during processing.

The novel sulfonamides of this invention are aromatic bis-sulfonamides containing in the molecule at least two bromoaromatic groups (preferably two or three), from 18 to 30 carbon atoms (preferably 18 to 24), and from 6 to 14 bromine atoms substituted on the aromatic rings. The presence of such bromine ring substituents tends greatly to enhance the thermal stability and flame retardant characteristics of the compound.

Among the polybromoaromatic bis-sulfonamides of this invention are those represented by the general formula

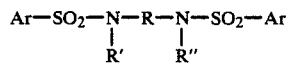

where Ar are the same or different polybromoaromatic groups, R is a divalent aromatic or bromoaromatic group, and R' and R" are independently hydrogen atoms, hydrocarbon groups or halohydrocarbon groups in which the halogen atoms are preferably chlorine or, most preferably, bromine, the total number of bromine atoms substituted on the aromatic rings of the groups designated as Ar and R falling in the range of 6 to 14. Most preferably the two Ar groups each contain at least three bromine atoms on the ring, and R' and R" are identical to each other.

One preferred subgroup of aromatic bis-sulfonamides of this invention are compounds which may be represented by the general formula

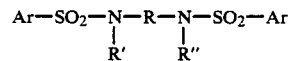

where each Ar group is a mononuclear aryl group having 6 to 10 carbon atoms and 3 to 5 bromine atoms on the aromatic ring, R is an arylene group having from 6 to 14 carbon atoms and optionally having from 1 to 4 bromine ring substituents, and R' and R" are identical to each other and are hydrogen or alkyl groups each having up to 18 carbon atoms, and preferably up to about 8 carbon atoms.

Another preferred subgroup of polybromoaromatic bis-sulfonamides of this invention are compounds represented by the general formula

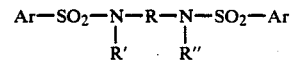

where each Ar group is a phenyl group having from 3 to 5 bromine atoms on the ring, R is a phenylene group optionally having 1 to 4 bromine atoms on the ring or a biphenylene group optionally having from 1 to 8 ring-substituted bromine atoms, and R' and R" are identical to each other and are hydrogen or alkyl groups each having up to 18 carbon atoms, and preferably up to about 8 carbon atoms.

Still another preferred subgroup of bromine-containing aromatic bis-sulfonamides utilized pursuant to this invention are compounds which may be represented by the general formula

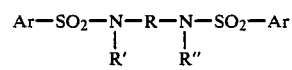

where each Ar group is a mononuclear aryl group having 6 to 10 carbon atoms and from 3 to 5 bromine atoms on the ring, R is an arylene group having from 6 to 10 carbon atoms, and R' and R" are identical to each other and are hydrogen or alkyl groups each having up to 18 carbon atoms, and preferably up to about 8 carbon atoms.

A few illustrative compounds of this invention include
N,N'-o-phenylenebis(tribromobenzenesulfonamide),
N,N'-o-phenylenebis(tetrabromobenzenesulfonamide),
N,N'-o-phenylenebis(pentabromobenzenesulfonamide),
N,N'-p-phenylenebis(tribromobenzenesulfonamide),
N,N'-p-phenylenebis(tetrabromobenzenesulfonamide),
N,N'-p-phenylenebis(pentabromobenzenesulfonamide),
N,N'-m-phenylenebis(tribromobenzenesulfonamide),
N,N'-p-(bromophenylene)bis(tribromobenzenesulfonamide),
N,N'-p-(dibromophenylene)bis(tribromobenzenesulfonamide),
N,N'-p-(tribromophenylene)bis(tribromobenzenesulfonamide),
N,N'-p-(tetrabromophenylene)bis(tribromobenzenesulfonamide),
N,N'-p-(tetrabromophenylene)bis(tetrabromobenzenesulfonamide),
N,N'-p-(tetrabromophenylene)bis(pentabromobenzenesulfonamide),
N,N'-p-(dibromophenylene)bis(tribromotoluenesulfonamide),
N,N'-p-(dibromophenylene)bis(2,5-dibromo-4-ethylbenzenesulfonamide),
N,N'-(1,2,3,4-tetrahydro-1,4-naphthalenediyl)bis(tribromobenzenesulfonamide),
4',4'''-(2,2'',4,4'',5,5''-hexabromo)bi[benzenesulfonanilide],
N,N'-(9,10-dihydro-9,10-anthracenediyl)bis[N-methyltribromobenzenesulfonamide), benzenesulfonamide),
N,N'-(9,10-dihydro-9,10-anthracenediyl)bis[tetrabromo-N-ethylbenzenesulfonamide),
N,N'-p-(bromophenylene)bis(tribromoxylenesulfonamide),
N,N'-p-(2,5-xylylene)bis(2,3,4,5-tetrabromobenzenesulfonamide),
N,N'-p-phenylenebis(pentabromobenzenesulfonamide), and
N,N'-(dibromoxylylene)bis(tribromobenzenesulfonamide).

General methods which can be adapted and utilized for the preparation of the compounds of this invention are known and reported in the literature. The most common procedure is to react a polybromoaromatic sulfonyl halide with an appropriate aromatic diamine.

Alternatively an aromatic bis-sulfonamide may be subjected to bromination under usual conditions for effecting substitutive ring halogenation of aromatic hydrocarbons. For further details concerning applicable synthesis procedures, see for example El-Hewehi, et al., *J. Prakt. Chem.*, 1962, Vol 5–6, 297–336 and El-Hewehi, et al., *J. Prakt. Chem.*, 1966. Vol. 34 No. 5–6, 218–242, all disclosures of which are incorporated herein by reference.

A wide variety of thermoplastic polymers may be used in forming the polymer compositions of this invention. Included are such thermoplastics as polyamides (all types of nylons such as nylon 6, nylon 6,6, etc.), polyesters (e.g., polyethylene terephthalate, polybutylene terephthalate, etc.), polycarbonates, polyolefins (e.g., polyethylenes, polypropylenes, etc.), polystyrenes (both rubber-free and rubber-modified), and the like.

The concentration of the polybromoaromatic bissulfonamides used will of course dependent to some extent upon the identity and properties of the substrate thermoplastic polymer and of the particular additive system being employed therein, as well as the properties desired in the finished product. Generally speaking, the polymer will normally contain an amount of the bis-sulfonamide falling in the range of from about 1 to about 20, and preferably from about 2 to about 10, parts by weight per hundred parts by weight of the total thermoplastic composition. However departures from these ranges are entirely permissible and are within the ambit of this invention. Those skilled in the art can readily determine optimal proportions by the simple expedient of performing a few simple tests with the materials selected for use.

Methods for blending the additives into the substrate polymers are conventional and well known to those skilled in the art.

Other conventionally used additives such as reinforcing fillers, pigments, mold release agents, nucleating agents, flame retardants, flame retardant synergists (antimony oxide, zinc borate, etc.), heat stabilizers, and the like may be included in the compositions of this invention. Such additives may be employed in their customary concentrations.

This invention is susceptible to considerable variation in its practice within the spirit and scope of the appended claims.

What is claimed is:

1. A polybromoaromatic bis-sulfonamide containing in the molecule at least two bromoaromatic groups, from 18 to 30 carbon atoms (preferably 18 to 24), and from 6 to 14 bromine atoms substituted on the aromatic rings, said polybromoaromatic bissulfonamide being represented by the general formula

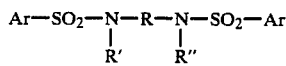

where Ar are the same or different polybromoaromatic groups, R is a divalent aromatic or bromoaromatic group, and R' and R" are independently hydrogen atoms, hydrocarbon groups or halohydrocarbon groups in which the halogen atoms are chlorine or bromine, the total number of bromine atoms substituted on the aromatic rings of the groups designated as Ar and R falling in the range of 6 to 14.

2. A compound of claim 1 in which the two Ar groups each contains at least three bromine atoms on the ring, and R' and R" are identical to each other.

3. A compound of claim 1 in which R' and R" are both hydrogen atoms.

4. A compound of claim 1 in which R is a phenylene group.

5. A compound of claim 1 in which R is a bromophenylene group.

6. An aromatic bis-sulfonamide represented by the general formula

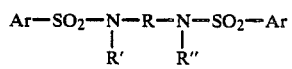

where each Ar group is a mononuclear aryl group having 6 to 10 carbon atoms and 3 to 5 bromine atoms on the aromatic ring, R is an arylene group having from 6 to 14 carbon atoms and optionally having from 1 to 4 bromine ring substituents, and R' and R" are identical to each other and are hydrogen or alkyl groups each having up to about 8 carbon atoms.

7. An aromatic bis-sulfonamide represented by the general formula

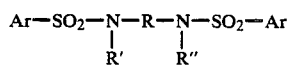

where each Ar group is a phenyl group having from 3 to 5 bromine atoms on the ring, R is a phenylene group optionally having 1 to 4 bromine atoms on the ring or a biphenylene group optionally having from 1 to 8 ring-substituted bromine atoms, and R' and R" are identical to each other and are hydrogen or alkyl groups each having up to about 8 carbon atoms.

8. An aromatic bis-sulfonamide represented by the general formula

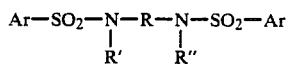

where each Ar group is a mononuclear aryl group having 6 to 10 carbon atoms and from 3 to 5 bromine atoms on the ring, R is an arylene group having from 6 to 10 carbon atoms, and R' and R" are identical to each other and are hydrogen or alkyl groups each having up to about 8 carbon atoms.

* * * * *